(12) United States Patent
Wolf et al.

(10) Patent No.: US 7,613,509 B2
(45) Date of Patent: Nov. 3, 2009

(54) SYSTEMS, METHODS, AND COMPUTER PROGRAM PRODUCTS FOR TRANSMITTING NEURAL SIGNAL INFORMATION

(75) Inventors: Patrick D. Wolf, Durham, NC (US); Iyad Obeid, Brussels (BE)

(73) Assignee: Duke University, Durham, NC (US)

( * ) Notice: Subject to any disclaimer, the term of this patent is extended or adjusted under 35 U.S.C. 154(b) by 282 days.

(21) Appl. No.: 10/998,385

(22) Filed: Nov. 29, 2004

(65) Prior Publication Data

US 2006/0116738 A1 Jun. 1, 2006

(51) Int. Cl.
*A61B 5/0484* (2006.01)
(52) U.S. Cl. ...................... 600/545; 600/544
(58) Field of Classification Search ............. None
See application file for complete search history.

(56) References Cited

U.S. PATENT DOCUMENTS 6,146,335 A * 11/2000 Gozani .................. 600/554
6,366,813 B1 * 4/2002 DiLorenzo .............. 607/45
2004/0138579 A1 * 7/2004 Deadwyler et al. ........ 600/544

* cited by examiner

Primary Examiner—Kennedy J Schaetzle
(74) Attorney, Agent, or Firm—Jenkins, Wilson, Taylor & Hunt, P.A.

(57) ABSTRACT

Systems, Methods, and Computer Program Products for Transmitting Neural Signal Information. Systems, method, and computer program products are provided for neural signal transmission. A system according to one embodiment can include a signal receiver operable to receive a neural signal comprising an action potential. The system can also include an action potential detector operable to communicate with the signal receiver and detect when the action potential occurs. In addition, the system can include a transmitter in communication with the action potential detector and operable to transmit an information signal indicating the time when the action potential occurs and, in addition, can transmit samples associated with a detected action potential.

66 Claims, 5 Drawing Sheets

SYSTEMS, METHODS, AND COMPUTER PROGRAM PRODUCTS FOR TRANSMITTING NEURAL SIGNAL INFORMATION

GRANT STATEMENT

This invention was supported by DARPA grant N66001-02-C-8022. Thus, the Government has certain rights in this invention.

TECHNICAL FIELD

The subject matter disclosed herein relates generally to neural signal processing. Specifically, the subject matter disclosed herein relates to systems, methods, and computer program products for transmitting neural signal information.

BACKGROUND ART

The human brain is an exceedingly complex processing system, which integrates continual streams of incoming sensory input data with stored memories, uses the input data and memories in complex decision processes at both conscious and unconscious levels and, on the basis of these processes, generates observable behaviors by activation of its motor or movement control pathways and the muscles which these innervate. The neurons of the nervous system propagate input data by generating characteristic electrical pulses called action potentials (APs), or neural spikes, that can travel along nerve fibers. A single neuron or a group of neurons represent and transmit information by firing sequences of APs in various temporal patterns. Information is carried in the AP arrival times.

In certain cases of traumatic injury or neurological disease, the brain can be partially isolated from the periphery. Input data from certain senses are thus lost, at least for a portion of the body, as are many voluntary movements. Spinal cord injury is a well-known example of traumatic injury. With spinal cord injury, the pathways that link higher motor centers in the brain with the spinal cord and that are used for control of voluntary movements can be functionally transected at the site of the injury. As a result, the patient is paralyzed, and can no longer voluntarily activate muscles that are innervated by regions of the spinal cord below the level of the injury. Despite the injury to their long fibers, however, many of the cells in these higher brain regions that control voluntary movement will survive and can still be activated voluntarily to generate electric signals for controlling voluntary movement. By recording the electrical activities produced from these cells with implantable neural sensors (e.g., a microwire electrode array, a microwire, a magnetic field detector, chemical sensor, or other neural sensor), signals generated by the cells can be "exteriorized" and used for the control of external prostheses, such as an assist robot or an artificial limb, or functional electrical stimulation of paralyzed muscles. Additionally, these generated signals can be used for control of computer operations such as the movement of a cursor on a computer display.

Technology is now emerging that will allow prosthetic limbs to be controlled directly and unconsciously by the brain. If the brain signals normally used for controlling limbs can be harnessed, they can be used to control "neuroprosthetic" limbs. The technology required for interfacing recording hardware into the brain is known as the brain-machine interface (BMI). For BMIs to be effective, they must wirelessly transmit neural information to a processor that controls the prosthesis. Since information content scales with the number of recorded neurons, it is desirable to increase the number of electrodes that the BMI can monitor. However, limitations in available wireless technologies restrict the number of neural electrodes that can be monitored simultaneously.

Based on the above limitations in neural action potential signaling, it is desired to provide improved systems and methods for transmitting a signal indicating detection of a neural action potential. It is also desirable to provide improved technology for increasing the number of electrodes that can be monitored. Further, it is desirable to compress the useful neural signal data prior to transmission.

SUMMARY

Systems, method, and computer program products are disclosed for neural signal transmission. A system according to one embodiment can include a signal receiver operable to receive a neural signal comprising an action potential. The system can also include an action potential detector operable to communicate with the signal receiver and detect when the action potential occurs. In addition, the system can include a transmitter in communication with the action potential detector and operable to transmit an information signal indicating the time when the action potential occurs.

Some of the objects having been stated hereinabove, and which are achieved in whole or in part by the present subject matter, other objects will become evident as the description proceeds when taken in connection with the accompanying drawings as best described hereinbelow.

BRIEF DESCRIPTION OF THE DRAWINGS

Exemplary embodiments of the subject matter will now be explained with reference to the accompanying drawings, of which.

DETAILED DESCRIPTION OF THE INVENTION

I. Definitions

Figure 1:
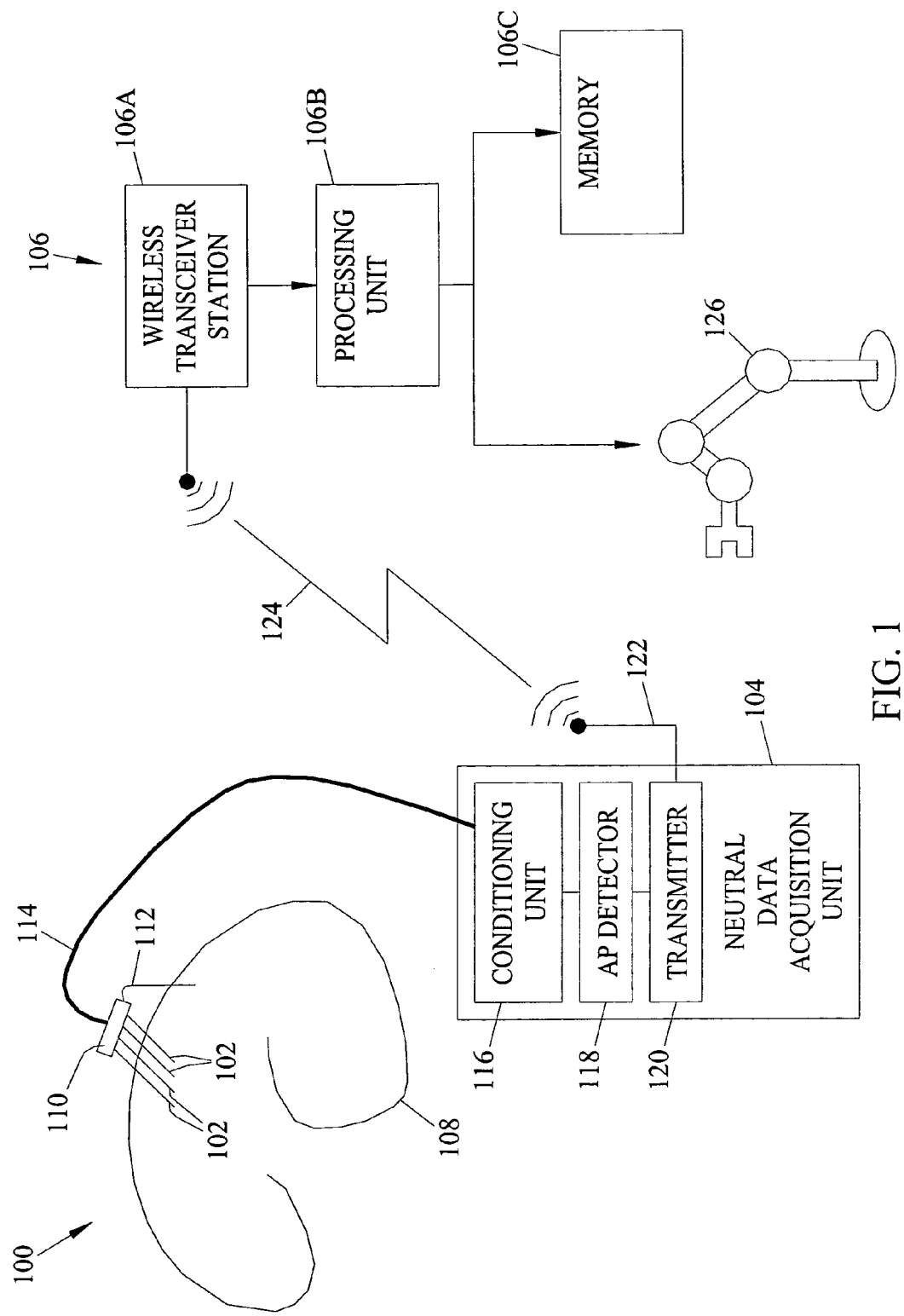
FIG. 1 is a schematic view of a neural signal transmission system.

Following long-standing patent law convention, the terms "a" and "an" mean "one or more" when used in this application, including the claims.

As used herein, the terms "action potential", "AP", and "neural spike" mean the characteristic electrical pulses that can travel along nerve fibers.

As used herein, the terms "actuator", "external device" and "prosthetic limb" are used interchangeably and mean any kind of device adapted to perform a movement. Although an actuator preferably performs a movement in three dimensions, an actuator can also be limited to performing movements in two dimensions. Thus, an actuator can be a manipulandum confined to two-dimensional motion. A representative actuator comprises a prosthetic limb, which can be fitted on, or integrated into, the body of a subject. An actuator can also be associated with machinery and/or circuitry that allow the actuator to respond to one or more forms of input with one or more movements. In one example, the range of motion of an actuator designated as a substitute for a patient's lost or paralyzed limb is limited to the range of motion of the limb for which the actuator is substituting.

As used herein, the terms "field potential data" and "field potentials" are used interchangeably and typically mean low frequency, voltage measurements collected from one or more location sources near or at one or more neurons in a subject's brain or nervous system.

As used herein, the term "integrated circuit" refers to a small-scale, electronic device densely packaged with more than one integrated, electrical component. The components are manufactured on the surface of semiconductor material. There are various scales of integrated circuits that are classified based on the number of components per surface area of the semiconductor material, including small-scale integration (SSI), medium-scale integration (MSI), large-scale integration (LSI), very large-scale integration (VLSI), ultra large-scale integration (ULSI).

As used herein, the term "location source" means a position wherein a neural sensor can detect one or more neural signals.

As used herein, the term "neural signal" means a signal, which can take any form, originating in the nervous system of an organism. Neural signals typically include neural spike signals that carry information in their arrival times at destination neurons.

As used herein, the term "neural sensor" means an implantable device for sensing neural signals. Examples of neural sensors include microwire electrode arrays, optical sensors, microwires, magnetic field detectors, chemical sensors, and other suitable neural sensors which are known to those of skill in the art upon consideration of the present disclosure.

As used herein, the terms "operator," "patient" and "subject" are used interchangeably and mean any individual monitoring or employing the present invention, or an element thereof. Operators can be, for example, researchers gathering data from an individual, an individual who determines the parameters of operation of the present invention or the individual in or on which a high-density multichannel microelectrode array is disposed. Broadly, then, an "operator," "patient" or "subject" is one who is employing the present invention for any purpose. As used herein, the terms "operator," "patient" and "subject" need not refer exclusively to human beings, but rather the terms encompass all organisms having neural tissue, such as monkeys, dogs, cats, rodents, etc.

II. General Considerations

Through the years there has been significant research in the area of detecting and observing various electric potentials generated within the human body for medical diagnosis, biofeedback control of mental and physical states, and control of external devices. It is known that different regions of the brain are used to control different parts of the body and to process different sensory inputs. It is also known that when a human performs a certain function, such as moving an extremity or listening to a particular sound, multiple regions of the brain generate electrical action potentials to accomplish that function. It is also known that direct electrical stimulation of a particular region of the brain can cause at least partial reproduction of the functions or sensory input normally associated with that region of the brain. Determining which portions of a patient's brain are responsible for certain motor activities or certain sensory functions has become known as brain "mapping." After a patient's brain has been mapped, the mapping information can be exploited in a number of ways.

For example, it is possible to determine which portions of a patient's brain are responsible for processing signals associated with the movement of an extremity. Once a neurologist knows which portions of the patient's brain are responsible for processing these signals, it is possible to electrically stimulate selected portions of the patient's brain to cause the patient to "move" the extremity. Similarly, a patient whose motor control has been partially or permanently damaged can regain motor control if an apparatus is employed to translate these neural signals into movement of an external device, such as an actuator or prosthetic device. Also, if the areas of the patient's brain that are associated with tactile and other sensory information are known, these areas of the patient's brain can be electrically stimulated to make the patient "experience" the sensory interaction between an object and an external device interacting with the object. Systems according to the present invention can be employed as a component of a system such as a closed loop brain-machine interface or intelligent brain pacemaker. These devices can greatly enhance the quality of life of individuals those individuals whose motor control has been impaired. Examples of brain machine interfaces and related systems are described in U.S. patent application Ser. No. 10/012,012, entitled "Closed Loop Brain Machine Interface"; U.S. patent application Ser. No. 10/004,457, entitled "Intelligent Brain Pacemaker for Real-Time Monitoring and Controlling of Epileptic Seizures", U.S. patent application Ser. No. 10/097,312, entitled "Miniaturized High-Density Multichannel Electrode Array for Long-Term Neuronal Recordings"; and U.S. patent application Ser. No. 10/692,235, entitled "Apparatus for Acquiring and Transmitting Neural Signals and Related Methods", the disclosures of which are incorporated herein by reference in their entirety.

Neural signals typically consist of discrete neural action potentials (APs) interspersed over background noise from far-field neurons. Information is contained in the duration of the intervals between APs and the AP waveform shapes. Therefore, because such useful information is interspersed, the transmission of neural signals of interest may be improved by transmitting only the timing between APs and the AP waveform shapes. The subject matter disclosed herein discloses systems, methods, and computer program products for detecting APs and then transmitting only the associated spike waveform shapes and their arrival times. By transmitting data only when APs are detected (and not during periods of inactivity) the required data rate per channel can decrease by as much as a factor of 50.

III. Configuration and Operation of the Neural Action Potential Detection System Efficient methods, systems, and computer program products are disclosed herein for transmitting neural signal information. The neural action potentials can be detected in neural signals received from neural tissues, for example neural tissue of the brain or central nervous system. The system can include a neural sensor for receiving a neural signal comprising: (1) an action potential; (2) an action potential detector for detecting when the action potential occurs in the neural signal; and (3) a transmitter for transmitting an information signal indicating the time when the action potential occurs. The information signal can be received by a host station or computer for use in controlling an external device, such as an actuator, prosthetic device, or computer system, or to treat a neurological condition. The systems, methods, and computer program products will be explained in the context of flow charts and diagrams. It is understood that the flow charts and diagrams can be implemented in hardware, software, or a combination of hardware and software. Thus, the present invention can include computer program products comprising computer-executable instructions embodied in computer-readable media for performing the steps illustrated in each of the flow charts or implementing the devices illustrated in each of the diagrams.

FIG. 1 is a schematic view of a neural signal transmission system, generally designated 100, according to one embodiment. Broadly, system 100 includes the following main modules: a plurality of neural sensors 102, a neural data acquisition unit 104, and a signal processing unit (generally designated 106). System 100 can be worn by a subject, such as a human or monkey.

While in operation, neural sensors 102 and neural data acquisition unit 104, described in more detail below, can detect neural activity in the form of field potential data generated from neural tissue (e.g., from large numbers of single neurons) in a subject brain 108. Neural sensors 102 can comprise microwire bundles or integrated silicon arrays. Neural sensors 102 and neural data acquisition unit 104 can convert the field potential data to an electrical-based representation of the neural signal that is suitable for processing by the hardware and/or software of system 100. Neural sensors 102 can be implanted in brain 108 for detecting field potential data of the neural signals of interest. Neural sensors 102 can be secured to a skull via a connector in a headcap 110.

In one embodiment, neural sensors 102 can be positioned in different location sources in the subject for converting the field potential data detected from different neurons into electrical-based neural signals. A low-impedance electrode 112 can be used as a voltage reference for neural sensors 102. System 100 can be compatible with unipolar and bipolar signals. Unipolar signals are referenced to low-impedance electrode 112. Bipolar signals are referenced to one another. According to another embodiment, the signals of each neural sensor 102 can be processed (e.g., amplified and filtered) and digitized sequentially in a round-robin manner. Neural signals from neural sensors 102 and electrode 112 can be transmitted to acquisition unit 104 via a short cable 114.

Acquisition unit 104 can receive one or more neural signals on one or more communication channels from neural sensors 102 for detecting the occurrence of an AP in any of the neural signals. A channel can contain the electrical signal from a single neural sensor 102 or in the case of bipolar signals, from two neural sensors. Initially, the received neural signals can be conditioned with buffering and filtering by a conditioning unit 116 to remove unwanted in-band and out-of-band signal noise, such as field potential data detected from signals of other bioelectric generators in the subject. These sources include the heart (ECG), muscles (EMG), and signals from the effect of mechanical movement of the sensor in response to blood pressure, respiration, and physical motion.

Acquisition unit 104 can also include a neural action potential (AP) detector 118 for detecting the presence of action potentials (APs) in the neural signals of each channel. According to one embodiment, system 100 can receive data on 16 channels, digitize the data, and store the most recent 64 eight-bit samples from each of the 16 channels in a 1024×8 bit memory. As each sample is acquired, its absolute value can be taken using a 256×8 bit lookup table and the absolute value can be compared to a threshold value that has been previously determined for the current channel. If the absolute value of the sample exceeds the threshold, then an AP has been detected. The threshold for each channel can be determined by scaling the mean of 512 consecutive transformed samples for the particular channel by an integer multiplier. New thresholds can be computed once every 60 seconds or immediately following a system reset. After a delay of 35 samples from AP detection, 45 samples can be read from the memory, wherein 10 samples are pre-threshold and 35 samples are post-threshold. The samples read from the memory can then be sent to a First-In First-Out (FIFO) memory for buffering until a transmitter 120 can transmit the samples associated with the detected AP to signal processing unit 106.

Figure 2:
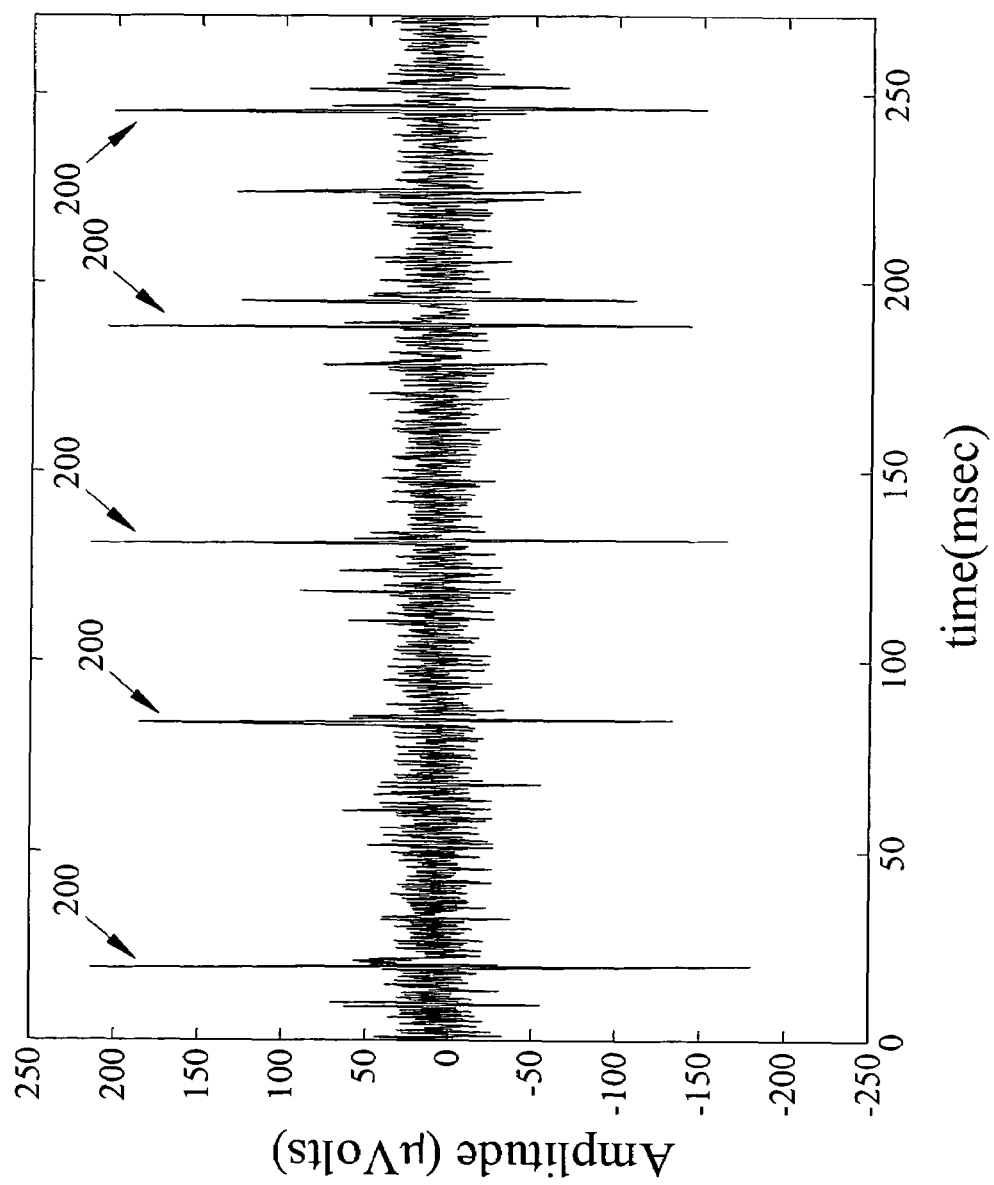
FIG. 2 is a timing diagram of an exemplary neural signal waveform.

Upon detecting an AP, transmitter 120 can transmit data associated with AP detection only on the detection of an AP. By transmitting data only on AP detection, the transmission data rate for each channel can be reduced because unwanted data between the occurrences of an AP is not transmitted. For example, FIG. 2 illustrates a timing diagram of an exemplary neural signal waveform. The information content of neural signals is encoded in the duration of the intervals between APs, generally designated 200. Therefore, it is inefficient to transmit the noise data between APs 200. Referring again to FIG. 1, transmitter 120 can be operable to transmit only those data samples corresponding to APs 200. In one embodiment, transmitter 120 can include a wireless telemetry unit for wirelessly transmitting data to signal processing unit 106 via a transceiver 122 on a transmission link 124. Alternatively, transmitter 120 can transmit data to signal processing unit 106 via a wire connection (not shown).

According to one embodiment, an AP identifier can be transmitted in association with the data samples associated with each AP detection. The AP identifier can comprise a channel number and a timestamp. The channel number can indicate the channel originating the data samples. The timestamp can indicate the time of the AP detection. Further, information indicating the waveform shape associated with the detected AP can be transmitted.

A wireless transceiver station 106A of signal processing unit 106 can receive the transmitted data on transmission link 124 from acquisition unit 104 and pass the data to a signal processing unit 106B. Signal processing unit 106B can perform processing such as AP sorting, binning of the timestamp data, and generating control signals based on the information signals. The processed neural data can be saved in a memory 106C for analysis purposes. In addition, the generated control signals can be used to control a prosthetic device 126. Further, the control signals can be used to control an actuator, prosthetic device, computer system, or other suitable device.

Figure 3:
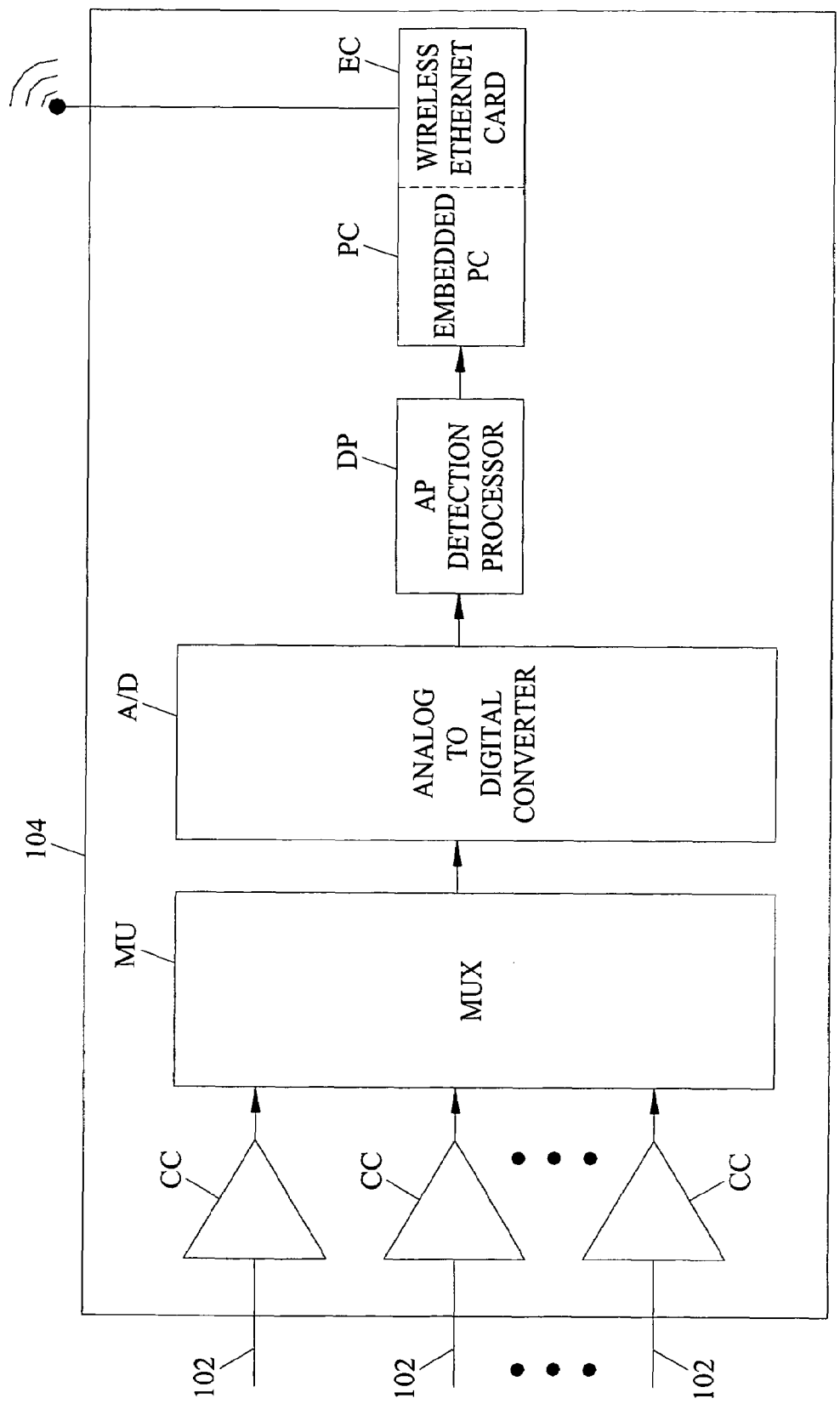
FIG. 3 is a block diagram illustrating an exemplary neural data acquisition unit according to one embodiment.

FIG. 3 is a block diagram illustrating an exemplary neural data acquisition unit 104 according to one embodiment. Acquisition unit 104 can be connected to a plurality of neural sensors 102 for receiving an analog, electrical-representation of neural signals from a subject. According to one embodiment, acquisition unit 104 can receive neural signals from 16 implanted neural sensors that each correspond to a monitored channel. Conditioning circuitry 104 can amplify and filter the received signals for improving the dynamic range of the signals and attenuating unwanted offset voltages and unwanted noise.

The conditioned signals can be passed to a multiplexer MU for multiplexing. According to one embodiment, MU is a 16:1 multiplexer. An analog-to-digital converter A/D can be connected to MU for sequentially selecting channels from MU and digital sampling. The digitized signal samples of the neural signals can therefore be produced at a rate of F samples per second per channel.

The digitized signal samples can then be transmitted to an AP detection processor DP for determining the absolute value of each incoming signal sample. In addition, processor DP can compare the absolute value for each signal sample to a previously calculated threshold to determine when AP occur in each channel. The samples from detected AP waveforms can then be passed to an embedded personal computer PC comprising IEEE standard 802.11b wireless Ethernet card EC for wireless transmission. Alternative to PC and Ethernet card EC, any suitable electronic component for wirelessly transmitting signals can be used.

Figure 4:
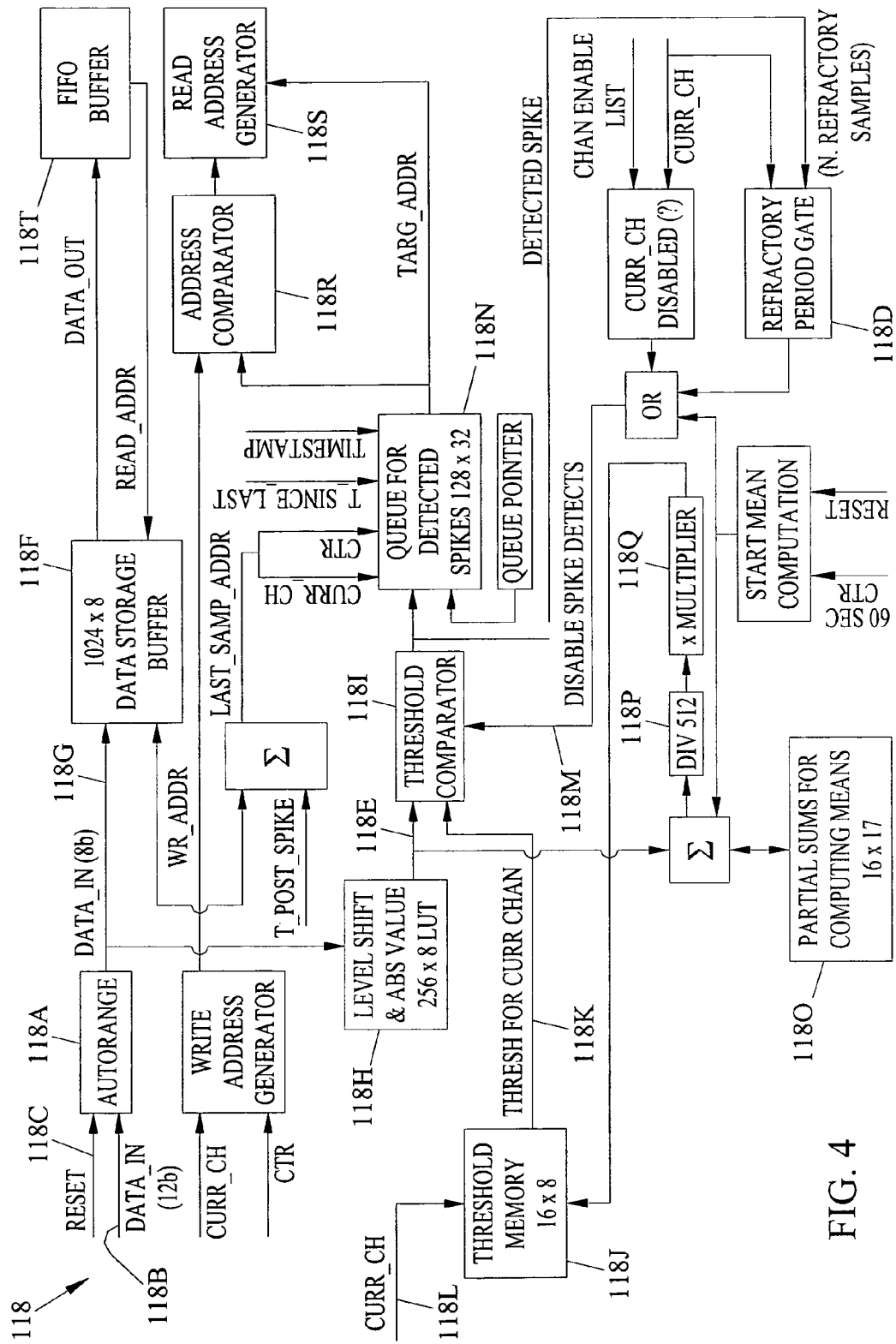
FIG. 4 is a schematic diagram illustrating an action potential (AP) detector.

FIG. 4 is a schematic diagram illustrating AP detector, generally designated 118. According to one embodiment, AP detection processor DP (FIG. 3) can comprise AP detector 118. AP detector 118 can implement a process for detecting and timestamping APs of a plurality of neural signals. The process can be implemented in a combination of software and/or hardware. According to one embodiment, the process can be implemented on a XILINX® XC2S100 Field Programmable Gate Array (FPGA) microchip (available from Xilinx, Inc. of San Jose, Calif., U.S.A.) with Verilog Hardware Description Language (VHDL). Alternatively, the process can be implemented on any other suitable Programmable Logic Device (PLD) or suitable hardware known to those of skill in the art.

According to one embodiment, AP detector 118 is operable to sequentially receive digitized neural signals in the form of 12-bit data words that can each represent one of sixteen (16) neural signals. Alternatively, AP detector 118 can receive digitized neural signals in the form of any number of bit data words or any number of neural signals. The digitized neural signals can be produced by any suitable devices for producing a digitized neural signal such as conditioning circuitry 104, MUX MU, and A/D converter A/D (FIG. 3) as described above.

AP detector 118 can comprise an automatic range (autorange) module 118A for receiving the digitized neural signals on data line 118B. Autorange module 118A can determine which eight (8) bits of the twelve (12) bits of a received 12-bit word to keep for processing. Alternatively, autorange module 118A can determine any suitable number of bits to keep of any number-bit word. The range of autorange module 118A can be recalibrated at predetermined intervals, upon user command, or system reset via reset line 118C. Autoranging can reduce the data bandwidth required by AP detector 118 while retaining dynamic range. For instance, by selecting the optimal 8 out of 12 bits to process, an 8-bit processor can be built instead of a 12-bit processor, thus saving power and space in the detector. The autodetector can operate by sampling each signal and using the highest order eight bits to determine the range of signal on each channel. Utilizing this range data, the device can select the eight bits that best represent the signal. As each signal is processed for spike detection, the optimal eight bits for each channel can be shifted into the lowest order bits and all processing from that point forward can operate only these bits.

AP detector 118 can include a refractory period gate 118D. Refractory period gate 118D can consist of a 1-bit flag and a 6-bit counter for each channel. When a spike is detected by detector 118E, the counter can be initialized to a suitable refractory period and the flag bit for the appropriate channel set to indicate that a channel is in its refractory period. The counter value can be set to 40 sample periods. As each new sample is processed for each channel, the flag bit can be tested and if the flag bit is set, the detected event can be ignored and the counter can be decremented and tested. If the counter has reached zero, the flag bit for that channel can be cleared. If it is not zero, the next channel can be processed.

AP detector 118 can include a memory 118F for storing the sixty-four (64) most recent 8-bit samples from each of the 16 monitored channels. The 8-bit samples can be transmitted to memory 118F from autorange module 118A via a line 118G. Memory 118F can be a 1024×8 bit data storage buffer. Alternatively, memory 118F can be any other suitable size.

According to one embodiment, APs in the digitized neural signals can be detected by transforming the neural signals with the absolute value operator $S\{X[n]\}=|x[n]|$, and comparing the result to a predetermined threshold. An AP is detected when the absolute value exceeds the threshold or when the absolute value exceeds the threshold and it has been at least a refractory period since the last detected AP. Other methods of detecting AP can be implemented in place of the absolute value detector. These other methods generally process the signal samples individually or in sequential groups of samples. The other methods can include matched linear or non-linear filters, energy-based detection algorithms, template matching, wavelet transformation, or other suitable detection algorithms known to those of skill in the art. AP detector 118 can include a look-up table (LUT) 118H for determining the absolute value of each sample transmitted on line 118G. According to one embodiment, LUT 118H can be a 256×9 table for 256 possible 8-bit sample values. During operation, LUT 118H can subtract 128 from each sample for performing a level shift. Next, LUT 118H can determine the absolute value of the number that is the result of level shifting. This number can then be applied to the address lines that LUT 118H and the number stored at that address read out. The LUT can be preprogrammed so that values that represent the absolute value equivalent of the address are stored in each location. For instance, if the binary representation of the number 127 represented the actual number −1, then when the address number 127 was accessed, the number representing +1 would be read out, thus producing the absolute value. The absolute value can be output on line 118E for receipt by a threshold comparator 118I.

Threshold comparator 118I can compare the absolute value on line 118E to a predetermined threshold for the current channel. The predetermined threshold can be provided by threshold memory 118J via line 118K. The current channel can be indicated to threshold memory 118J via a current channel line 118L. Threshold comparator 118I can be disabled while new threshold values are computed or if the current channel is disabled. Threshold comparator 118I can be disabled via line 118M.

The threshold for each channel can be calculated by taking the mean of the absolute value of 512 consecutive samples and then scaling by an integer multiplier. To calculate the means, partial sums of the outputs from LUT 118H can be computed by a partial sum unit 118N and stored in a 16×17 bit memory 118O. When the partial sums are complete, they are divided by 512 (shifted by nine bits) by divider 118P and scaled by a four-bit integer multiplier 118Q. New means can be computed every 60 seconds and following system resets. In this way, thresholds can be proportional to non-stationary levels of background noise, and so are relatively immune to variations in noise levels. Other suitable statistical measures of the quiescent signal level can also be used to determine the thresholds. Examples include either a running average or a mean that uses a different number of samples than 512.

A "Start Mean Computation" block can be used to start the process within the device to calculate a new mean for each neural channel to use in setting the threshold. The calculation can be started at a scheduled interval of 60 seconds or can be started by another input signal derived from an outside source such as a user input or a reset signal or other internally derived signals.

A "Write Address Generator" module can be present that generates the storage address for a given data value as it is acquired. The address is calculated from the current channel value "CURR CHAN" and size of data buffer 118F.

The top summer module can add the fixed value T_POST_SPIKE, or the number of samples to be saved after the detection has been made, to generate a LAST_SAMP_ADDR value that is stored in partial sum unit 118N.

Partial sum unit 118N can be a block of memory that holds the last address value for all spikes that have been detected within the T_POST_SPIKE number of samples. These are all the spikes which have been detected but still have samples remaining to be collected.

The "OR" module can determine if the process of spike detection is active. The spike detection process is inactive when the CURR_CH is not in the CHAN_ENABLE_LIST or when the system is in the process of computing new threshold values for the channels. The CHAN_ENABLE_LIST can be set by a user or can be automatically determined by examining the characteristics to determine whether there are spikes present or whether the channel only contains noise. An algorithm that looks at the quality of the signal by examining the signal itself or that looks at the output of the detector to determine if noise is present. For instance, in the first case, the signal-to-noise ratio may be estimated and, in the second case, the number of spikes per unit time may be tabulated.

Each time that the samples associated with a spike have been successfully output, the QUEUE_POINTER can be incremented to advance to the next LAST_SAMP_ADDR stored in the partial sum unit 118N.

When an AP is detected on a channel, AP detector 118 can collect a predetermined number of additional samples from the channel. In addition, when an AP is detected, an AP identifier can be written into queue 118N. According to one embodiment, the AP identifier is 32 bits, and queue 118N is 128×32 bits. Each AP identifier can comprise one or more of the following: (1) an address to which the additional samples has been written to in memory 118F; (2) a counter indicating the number of samples since the previous AP detection; and (3) a timestamp indicating the arrival time of the AP. In one embodiment, the address can be a 10-bit address for addressing memory 118F, the counter can be 6 bits, and the timestamp can be 16 bits.

Referring to FIG. 4, when each new sample is acquired, an address comparator 118R can compare the address to which the current sample is being stored with the address field of the first 32-bit identifier in queue 118N. If the channels numbers match and the counter value differs by 35, then a read address generator 118S can read out the ten pre-AP samples and the 35 post-AP samples from memory 118D for the current AP in queue 118N. These pre-AP and post-AP samples can be written to a First-In First-Out (FIFO) buffer 118T for storage until transmitted via a transmitter (such as transmitter 104 shown in FIG. 1). In addition, a header can be written to FIFO buffer 118T for transmission with the associated AP samples. The header can identify the AP samples and include the following: (1) one byte indicating the channel number associated with the AP; and (2) two bytes for the timestamp. Alternatively, only the header can be transmitted to FIFO buffer 118T, rather than the header and the samples corresponding to the AP.

The system can be implemented in a number of physical configurations that each embody the same basic functionality. For development purposes, the system was developed to be carried by the subject in a back-mounted harness. This harness contains discrete electrical components encompassing all of the stages shown in FIG. 3 as well as batteries and power regulation hardware. Alternatively, various stages of FIG. 3 can be integrated into an application specific integrated circuit (ASIC) and implanted under the skin. This may reduce or eliminate the back-mounted electronics and limits risks of infection due to transcutaneous wires. For example, conditioning circuitry 104 (FIG. 3) and MUX MU (FIG. 3) can be integrated into a single ASIC for implantation under the skin at the site of electrode implant. Signals can be passed via a transcutaneous wire bundle to the external electronics for digitization, detection, and processing. Using the same analog ASIC, signals can pass through a subcutaneous wire to an implanted hermetically sealed can in the neck or torso containing discrete electronic components for digitization and transmission. Further, in one embodiment, the components shown in FIG. 3 can be integrated into a single microchip or chipset that can be implanted at the electrode site in the head of a subject. It is possible for more than one analog ASIC to communicate with a single set of digital circuitry, either integrated or discrete, or implanted or external.

Figure 5:
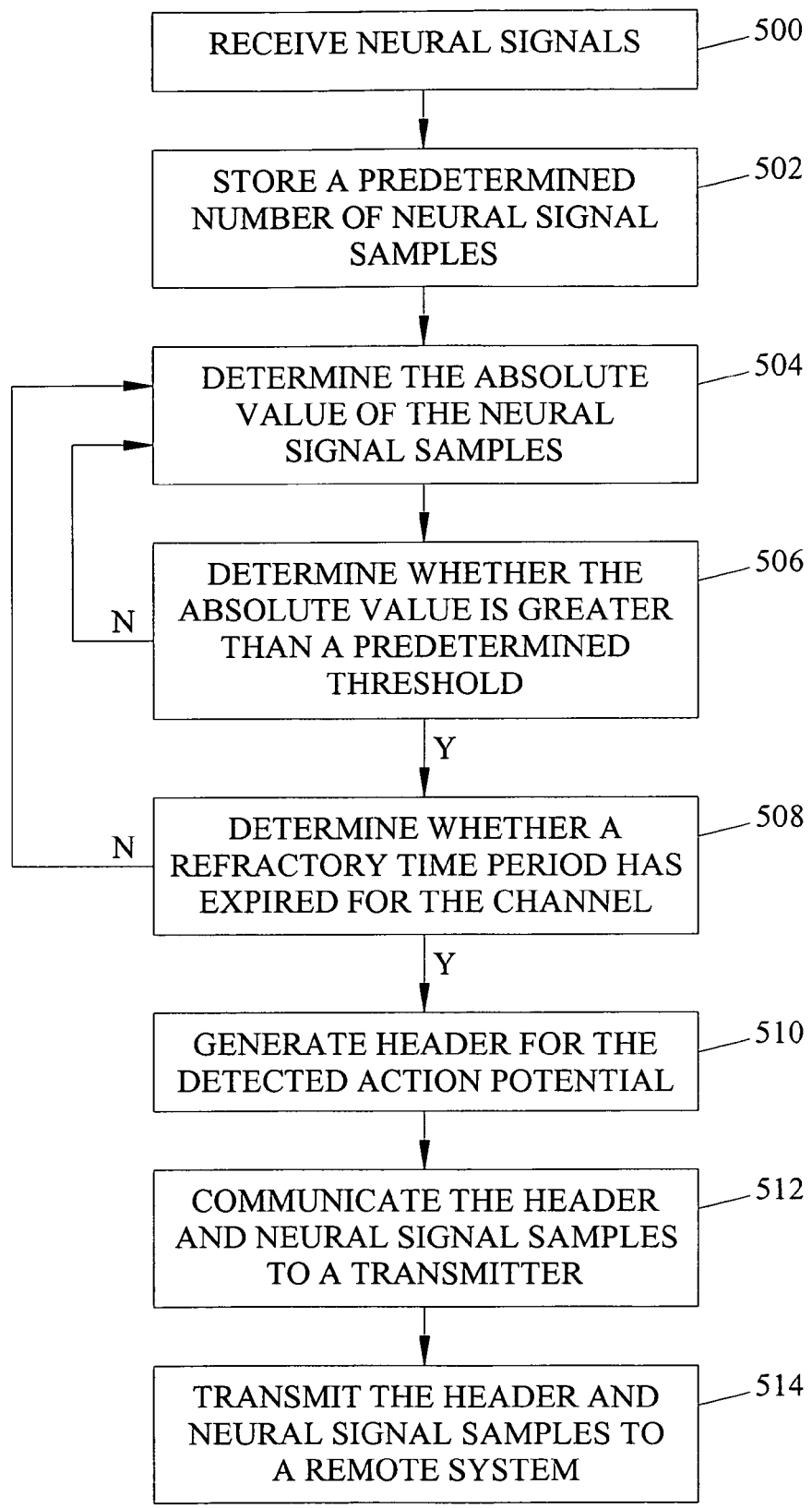
FIG. 5 is a flow chart illustrating an exemplary process for AP detection signaling according to one embodiment.

FIG. 5 is a flow chart illustrating an exemplary process for AP detection signaling according to one embodiment. As stated above, such AP detection signaling can be performed by AP detector 118 (FIG. 4). The process begins at the step indicated by reference numeral 500. At step 500, a plurality of neural signals are received by AP detector 118 (FIG. 4). Each neural signal can be received on a separate channel. Each channel can be identified with a channel number. In addition, AP detector 118 can store a predetermined number of the most recent samples of each neural signal (step 502).

Next, AP detector 118 can detect the occurrence of action potentials in the neural signals. Steps 504 and 506 are exemplary steps for detecting an action potential. At step 504, AP detector 118 can determine the absolute value of sequential samples of each neural signal. Next, at step 506, AP detector 118 can determine whether the absolute value is greater than a predetermined threshold. If the absolute value is not greater than the predetermined threshold, the process can return to step 504. If the absolute value is greater than the predetermined threshold, the process can proceed to step 508. At step 508, AP detector 118 can determine whether a refractory time period has expired for this channel, which can include determining whether this is the first sample to exceed the threshold since at least N_REFRACTORY_SAMPLES (step 508). If a refractory time period has not expired, the process can return to step 504. Otherwise, an action potential has been detected and the process can continue to step 510.

At step 510, a header can be generated for the detected action potential. The header can include the following information: (1) identification of the channel number associated with the detected action potential; and (2) a timestamp indicating when the action potential was detected. The header can be stored in a buffer for awaiting transmission.

At step 512, the header and neural signal samples associated with the detected action potential can be communicated to a transmitter such as transmitter 120 (FIG. 1). Next, at step 514, the transmitter can transmit the header and neural signal samples to a remote system such as signal processing unit 106 (FIG. 1). The transmitted information can be used by the remote system for controlling, for example, an actuator, a prosthetic device, or a computer system.

It will be understood that various details of the subject matter disclosed herein may be changed without departing from the scope of the subject. Furthermore, the foregoing description is for the purpose of illustration only, and not for the purpose of limitation.

What is claimed is:

1. A neural signal transmission system, comprising:
   (a) a signal receiver operable to receive a neural signal comprising an action potential, the neural signal represented by n-bit data samples;

(b) an action potential detector operable to communicate with the signal receiver, operable to determine an optimal range for the received neural signal, operable to select a subset of bits of the n-bit data samples based on the optimal range, operable to calculate a threshold value based on the neural signal, operable to compare the threshold value to the subset of bits of the neural signal, and operable to detect when the action potential occurs based on the comparison of the threshold value to the subset of bits of the neural signal; and (c) a transmitter in communication with the action potential detector and operable to transmit an information signal indicating the time when the action potential occurs.

2. The neural signal transmission system of claim 1 wherein the signal receiver is a neural sensor selected from the group consisting of electrodes, magnetic field detectors, and chemical sensors.

3. The neural signal transmission system of claim 1 comprising a plurality of signal receivers operable to receive a plurality of neural signals, wherein each signal receiver is associated with one of a plurality of channels.

4. The neural signal transmission system of claim 3 wherein the transmitter is operable to transmit a header associated with the action potential, wherein the header indicates the channel associated with the neural signal comprising the detected action potential.

5. The neural signal transmission system of claim 1 wherein the action potential detector is operable to transmit a header associated with the action potential, wherein the header comprises a timestamp indicating a time when the action potential occurs.

6. The neural signal transmission system of claim 1 wherein the action potential detector comprises a memory for storing samples of the neural signal.

7. The neural signal transmission system of claim 6 wherein the stored samples are a predetermined number of samples including the action potential of the neural signal.

8. The neural signal transmission system of claim 7 wherein a header associated with each neural signal indicates a channel associated with the neural signal.

9. The neural signal transmission system of claim 6 wherein the action potential detector is operable to determine an absolute value of one of the samples of the neural signal.

10. The neural signal transmission system of claim 9 wherein the action potential detector is operable to compare the absolute value to the threshold value.

11. The neural signal transmission system of claim 10 wherein the action potential detector detects an action potential when the absolute value is greater than the threshold value.

12. The neural signal transmission system of claim 10 wherein the action potential detector detects a first action potential after a refractory period expires since a second action potential, wherein the second action potential occurs prior to the first action potential and on the same channel.

13. The neural signal transmission system of claim 1 comprising a conditioning unit operable to condition the neural signal.

14. The neural signal transmission system of claim 13 wherein condition is a function selected from the group consisting of amplify, filter, multiplex, and digitize.

15. The neural signal transmission system of claim 1 comprising a station operable to receive the information signal for controlling a device selected from the group consisting of an actuator, a prosthetic device, and a computer system.

16. The neural signal transmission system of claim 1 wherein the action potential detector Is operable to:
    (i) determine a mean of absolute values of samples of the neural signal; and
    (ii) set the threshold value a scaled value of the determined mean.

17. The neural signal transmission system of claim 16 wherein the action potential detector Is operable to periodically determine the mean and set the threshold value.

18. The neural signal transmission system of claim 1 wherein the action potential detector Is operable to:
    (i) determine a mean of absolute values of derivatives of samples of the neural signal; and
    (ii) set the threshold value as a scaled value of the determined mean.

19. The neural signal transmission system of claim 1 wherein the action potential detector is operable to determine when a value of the neural signal exceeds the threshold value to detect when the action potential occurs.

20. The neural signal transmission system of claim 1 wherein the action potential detector is operable to compare the threshold value to an absolute value of the neural signal, and operable to detect when the action potential occurs based on the comparison of the threshold value to the absolute value of the neural signal.

21. The neural signal transmission system of claim 1 wherein the action potential detector is operable to compare the threshold value to an absolute value of derivatives of the neural signal, and operable to detect when the action potential occurs based on the comparison of the threshold value to the absolute value of the derivatives of the neural signal.

22. The neural signal transmission system of claim 1 wherein the transmitter is operable to wirelessly transmit the information signal.

23. A method for transmitting a neural signal, the method comprising:
    (a) receiving a neural signal comprising an action potential, the neural signal represented by n-bit data samples;
    (b) determining an optimal range for the received neural signal;
    (c) selecting a subset of bits of the n-bit data samples based on the optimal range;
    (d) calculating a threshold value based on the neural signal;
    (e) comparing the threshold value to the subset of bits of the neural signal;
    (f) detecting when the action potential occurs based on the comparison of the threshold value to the subset of bits of the neural signal; and
    (g) transmitting an information signal indicating the time when the action potential occurs.

24. The method of claim 23 wherein receiving a neural signal includes receiving the neural signal from a neural sensor.

25. The method of claim 23 comprising receiving a plurality of neural signals, wherein each signal is associated with one of a plurality of channels.

26. The method of claim 25 comprising transmitting a header associated with the action potential, wherein the header indicates the channel associated with the neural signal comprising the detected action potential.

27. The method of claim 23 comprising transmitting a header associated with the action potential, wherein the header comprises a timestamp indicating a time when the action potential occurs.

28. The method of claim 23 comprising storing samples of the neural signal.

29. The method of claim 28 wherein the stored samples are a predetermined number of samples including the action potential of the neural signal.

30. The method of claim 29 wherein a header associated with each neural signal indicates a channel associated with the neural signal.

31. The method of claim 28 comprising determining an absolute value of one of the samples of the neural signal.

32. The method of claim 31 comprising comparing the absolute value to the threshold value.

33. The method of claim 32 comprising detecting an action potential when the absolute value is greater than the threshold value.

34. The method of claim 32 comprising detecting a first action potential after a refractory period expires since a second action potential, wherein the second action potential occurs prior to the first action potential and on the same channel.

35. The method of claim 23 comprising conditioning the neural signal.

36. The method of claim 35 wherein the conditioning is a function selected from the group consisting of amplify, filter, multiplex, and digitize.

37. The method of claim 23 comprising receiving the information signal for controlling a device selected from the group consisting of an actuator, a prosthetic device, and a computer system.

38. The method of claim 23 wherein calculating a threshold value based on the neural signal comprises:
   (i) determining a mean of absolute values of samples of the neural signal; and
   (ii) setting the threshold value as a scaled value of the determined mean.

39. The method of claim 38 comprising periodically determining the mean and setting the threshold value.

40. The method of claim 23 wherein calculating a threshold value based on the neural signal comprises:
   (i) determining a mean of absolute values of derivatives of samples of the neural signal; and
   (ii) setting the threshold value as a scaled value of the determined mean.

41. The method of claim 23 comprising determining when a value of the neural signal exceeds the threshold value to detect when the action potential occurs.

42. The method of claim 23 wherein comparing the threshold value to the neural signal comprises comparing the threshold value to an absolute value of the neural signal, and wherein detecting when the action potential occurs comprises detecting when the action potential occurs based on the comparison of the threshold value to the absolute value of the neural signal.

43. The method of claim 23 wherein comparing the threshold value to the neural signal comprises comparing the threshold value to an absolute value of derivatives of the neural signal, and wherein detecting when the action potential occurs comprises detecting when the action potential occurs based on the comparison of the threshold value to the absolute value of the derivatives of the neural signal.

44. The method of claim 23 wherein transmitting an information signal comprises wirelessly transmitting the information signal.

45. A computer program product comprising computer-executable instructions embodied in a computer-readable medium for performing steps comprising:
   (a) receiving a neural signal comprising an action potential, the neural signal represented by n-bit data samples
   (b) determining an optimal range for the received neural signal;
   (c) selecting a subset of bits of the n-bit data samples based on the optimal range;
   (d) calculating a threshold value based on the neural signal;
   (e) comparing the threshold value to the subset of bits of the neural signal;
   (f) detecting when the action potential occurs based on the comparison of the threshold value to the subset of bits of the neural signal; and
   (g) transmitting an information signal indicating the time when the action potential occurs.

46. The computer program product of claim 45 wherein receiving a neural signal includes receiving the neural signal from a neural sensor.

47. The computer program product of claim 45 comprising receiving a plurality of neural signals, wherein each signal is associated with one of a plurality of channels.

48. The computer program product of claim 47 comprising transmitting a header associated with the action potential, wherein the header indicates the channel associated with the neural signal comprising the detected action potential.

49. The computer program product of claim 45 comprising transmitting a header associated with the action potential, wherein the header comprises a timestamp indicating a time when the action potential occurs.

50. The computer program product of claim 45 comprising storing samples of the neural signal.

51. The computer program product of claim 50 wherein the stored samples are a predetermined number of samples including the action potential of the neural signal.

52. The computer program product of claim 51 wherein a header associated with each neural signal indicates a channel associated with the neural signal.

53. The computer program product of claim 50 comprising determining an absolute value of one of the samples of the neural signal.

54. The computer program product of claim 53 comprising comparing the absolute value to the threshold value.

55. The computer program product of claim 53 comprising detecting an action potential when the absolute value is greater than the threshold value.

56. The computer program product of claim 53 comprising detecting a first action potential after a refractory period expires since a second action potential, wherein the second action potential occurs prior to the first action potential and on the same channel.

57. The computer program product of claim 45 comprising conditioning the neural signal.

58. The computer program product of claim 57 wherein the conditioning is a function selected from the group consisting of amplify, filter, multiplex, and digitize.

59. The computer program product of claim 45 comprising receiving the information signal for controlling a device selected from the group consisting of an actuator, a prosthetic device, and a computer system.

60. The computer program product of claim 45 wherein calculating a threshold value based on the neural signal comprises:
   (i) determining a mean of absolute values of samples of the neural signal; and
   (ii) setting the threshold value as a scaled value of the determined mean.

61. The computer program product of claim 60 comprising periodically determining the mean and setting the threshold value.

62. The computer program product of claim 45 wherein calculating a threshold value based on the neural signal comprises:

(i) determining a mean of absolute values of derivatives of samples of the neural signal; and (ii) setting the threshold value as a scaled value of the determined mean.

63. The computer program product of claim 45 comprising determining when a value of the neural signal exceeds the threshold value to detect when the action potential occurs.

64. The computer program product of claim 45 wherein comparing the threshold value to the neural signal comprises comparing the threshold value to an absolute value of the neural signal, and wherein detecting when the action potential occurs comprises detecting when the action potential occurs based on the comparison of the threshold value to the absolute value of the neural signal.

65. The computer program product of claim 45 wherein comparing the threshold value to the neural signal comprises comparing the threshold value to an absolute value of derivatives of the neural signal, and wherein detecting when the action potential occurs comprises detecting when the action potential occurs based on the comparison of the threshold value to the absolute value of the derivatives of the neural signal.

66. The computer program product of claim 45 wherein transmitting an information signal comprises wirelessly transmitting the information signal.

* * * * *

UNITED STATES PATENT AND TRADEMARK OFFICE
CERTIFICATE OF CORRECTION

| | | |
|---|---|---|
| PATENT NO. | : 7,613,509 B2 | Page 1 of 1 |
| APPLICATION NO. | : 10/998385 | |
| DATED | : November 3, 2009 | |
| INVENTOR(S) | : Wolf et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 601 days.

Signed and Sealed this

Nineteenth Day of October, 2010

David J. Kappos
*Director of the United States Patent and Trademark Office*